United States Patent
Kubo

(10) Patent No.: US 10,937,297 B2
(45) Date of Patent: Mar. 2, 2021

(54) SIGNAL RELAY APPARATUS AND PATIENT MONITORING SYSTEM

(71) Applicant: NIHON KOHDEN CORPORATION, Tokyo (JP)

(72) Inventor: Hiroshi Kubo, Tokorozawa (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 0 days.

(21) Appl. No.: 16/352,232

(22) Filed: Mar. 13, 2019

(65) Prior Publication Data

US 2019/0295399 A1 Sep. 26, 2019

(30) Foreign Application Priority Data

Mar. 22, 2018 (JP) .............................. JP2018-055108

(51) Int. Cl.
| | |
|---|---|
| *G08B 21/04* | (2006.01) |
| *A61B 5/00* | (2006.01) |
| *G16H 50/70* | (2018.01) |
| *G16H 40/63* | (2018.01) |
| *A61B 5/021* | (2006.01) |
| *A61B 5/024* | (2006.01) |
| *A61B 5/029* | (2006.01) |
| *A61B 5/0402* | (2006.01) |

(Continued)

(52) U.S. Cl.
CPC ........ *G08B 21/0453* (2013.01); *A61B 5/7235* (2013.01); *A61B 5/7425* (2013.01); *G16H 40/63* (2018.01); *G16H 50/70* (2018.01); *A61B 5/021* (2013.01); *A61B 5/024* (2013.01); *A61B 5/029* (2013.01); *A61B 5/0402* (2013.01); *A61B 5/0476* (2013.01); *A61B 5/14551* (2013.01); *A61B 5/7405* (2013.01)

(58) Field of Classification Search
None
See application file for complete search history.

(56) References Cited

U.S. PATENT DOCUMENTS

| | | | |
|---|---|---|---|
| 8,620,418 B1 * | 12/2013 | Kuppuraj | A61B 5/0404 600/523 |
| 2009/0231125 A1 | 9/2009 | Baldus et al. | |

(Continued)

FOREIGN PATENT DOCUMENTS

| | | |
|---|---|---|
| CN | 104582562 A | 4/2015 |
| JP | 2016-171965 A | 9/2016 |

OTHER PUBLICATIONS

Extended European Search Report issued in Patent Application No. EP 19 16 3115 dated Aug. 16, 2019.

*Primary Examiner* — Thomas S McCormack
(74) *Attorney, Agent, or Firm* — Pearne & Gordon LLP

(57) ABSTRACT

A patient monitoring system includes a patient monitor configured to display physiological information of a subject, and a signal relay apparatus configured to communicate with the patient monitor. The signal relay apparatus includes a sensor interface configured to receive a signal from a sensor attached to the subject, an analyzer configured to analyze the signal to acquire data corresponding to the physiological information, a communication interface configured to transmit at least one of the signal and the data to the patient monitor, and a controller configured to perform a notification when a display of the physiological information on the patient monitor meets a first abnormality condition.

18 Claims, 4 Drawing Sheets

(51) Int. Cl.
*A61B 5/0476* (2006.01)
*A61B 5/1455* (2006.01)

(56) References Cited

U.S. PATENT DOCUMENTS

| | | | |
|---|---|---|---|
| 2015/0205931 A1* | 7/2015 | Wang | G16H 40/63 |
| | | | 702/19 |
| 2018/0242925 A1* | 8/2018 | Sugawara | G06F 3/0488 |
| 2018/0333050 A1* | 11/2018 | Greiner | A61B 5/002 |

* cited by examiner

SIGNAL RELAY APPARATUS AND PATIENT MONITORING SYSTEM

CROSS-REFERENCE TO RELATED APPLICATION

The present application claims priority to Japanese Patent Application No. 2018-055108 filed on Mar. 22, 2018 the entire content of which is incorporated herein by reference.

BACKGROUND

The presently disclosed subject matter relates to a signal relay apparatus configured to relay signals corresponding to physiological information of a subject to a patient monitor. The presently disclosed subject matter also relates to a patient monitoring system including the signal relay apparatus and the patient monitor.

According to a related art patient monitoring system, various sensors are attached to a subject to acquire physiological information, and signals output from the sensors are first input to a signal relay apparatus, also called an input unit (see, e.g., JP2016-171965A). When the signal relay apparatus and a patient monitor are connected to each other, the signals from the sensors are input to the patient monitor through the signal relay apparatus. The patient monitor is configured to process and analyze the input signals, and to display the physiological information.

When the connection of the signal relay apparatus to the patient monitor is cancelled, and the signal relay apparatus is connected to another patient monitor disposed in a remote place, physiological information can be displayed on the other patient monitor. Namely, the use of the signal relay apparatus enables movement of the subject between different patient monitors without detaching the sensors from the body.

SUMMARY

Illustrative aspects of the presently disclosed subject matter enable monitoring of physiological information to be continued by using a signal relay apparatus, even in the case where physiological information is not properly displayed on a patient monitor.

According an illustrative aspect of the presently disclosed subject matter, a signal relay apparatus a signal relay apparatus includes a sensor interface configured to receive a signal from a sensor attached to a subject, an analyzer configured to analyze the signal to acquire data corresponding to physiological information of the subject, a communication interface configured to transmit at least one of the signal and the data to a patient monitor, and a controller configured to perform a first notification when a display of the physiological information on the patient monitor meets a first abnormality condition.

According another illustrative aspect of the presently disclosed subject matter, a patient monitoring system includes a patient monitor configured to display physiological information of a subject, and a signal relay apparatus configured to communicate with the patient monitor. The signal relay apparatus includes a sensor interface configured to receive a signal from a sensor attached to the subject, an analyzer configured to analyze the signal to acquire data corresponding to the physiological information, a communication interface configured to transmit at least one of the signal and the data to the patient monitor, and a controller configured to perform a notification when a display of the physiological information on the patient monitor meets a first abnormality condition.

According to the above-described configurations, the user who receives the notification can immediately take an action to continue monitoring of physiological information. Even in the case where physiological information is not properly displayed on the patient monitor, therefore, it is possible to enable monitoring of the physiological information of the subject to be continued by using the signal relay apparatus.

DETAILED DESCRIPTION

Figure 1:
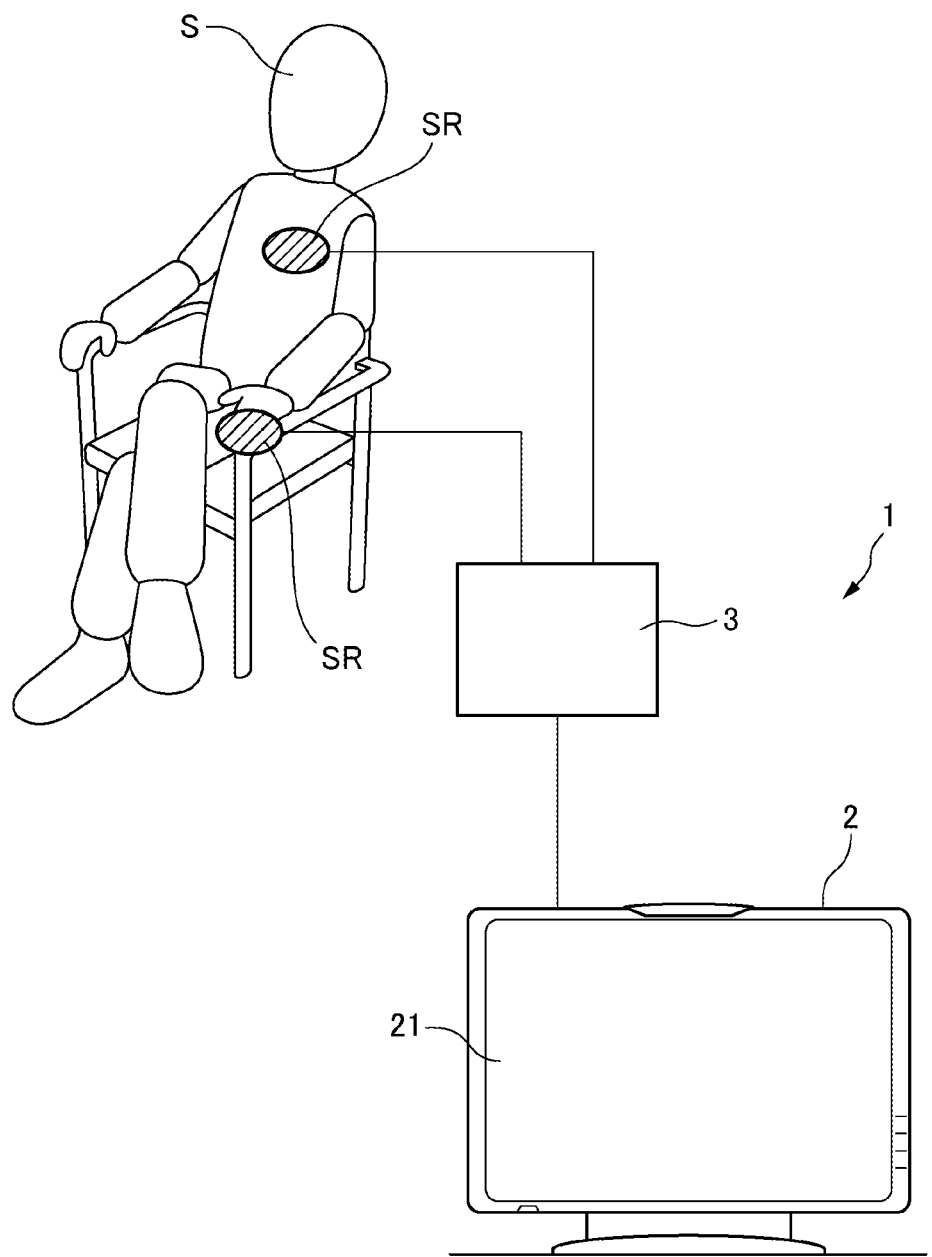
FIG. 1 illustrates a configuration of a patient monitoring system according to an embodiment of the presently disclosed subject matter.

Hereinafter, embodiments of the presently disclosed subject matter will be described in detail with reference to the accompanying drawings. In the drawings, in order to make the components to be described, to have a recognizable size, their scales are appropriately changed.

As illustrated in FIG. 1, a patient monitoring system 1 according to one embodiment of the presently disclosed subject matter may include a patient monitor 2 and a signal relay apparatus 3. Preferably, the signal relay apparatus 3 is a portable apparatus and is smaller and lighter than the patient monitor 2.

Various sensors SR for acquiring desired physiological information are attached to a subject S. Examples of the sensors SR include electrodes for acquiring an electrocardiogram, electrodes for acquiring brain waves, a cuff for acquiring a non-invasive blood pressure, a probe for acquiring the pulse rate, and a probe for acquiring a non-invasive arterial oxygen saturation ($SpO_2$).

Signals corresponding to physiological information are output from the respective sensors SR and input to the signal relay apparatus 3. The signal relay apparatus 3 and the patient monitor 2 are connected to each other such that they can communicate bidirectionally. The connection between the signal relay apparatus 3 and the patient monitor 2 may be performed in a wired or wireless manner. The signals output from the sensors SR are input to the patient monitor 2 through the signal relay apparatus 3.

The patient monitor 2 may include a display 21. Based on the signals supplied from the signal relay apparatus 3, the display 21 displays the corresponding physiological information.

In this description, the "physiological information" is defined as information on a condition of a physiological parameter in a form that can be recognized visually or audibly. Examples of physiological information include at least one of a waveform and a numerical value of at least one of physiological parameters such as an electrocardiogram, brains waves, non-invasive blood pressure, pulse rate, non-invasive arterial oxygen saturation ($SpO_2$), and cardiac output.

Figure 2:
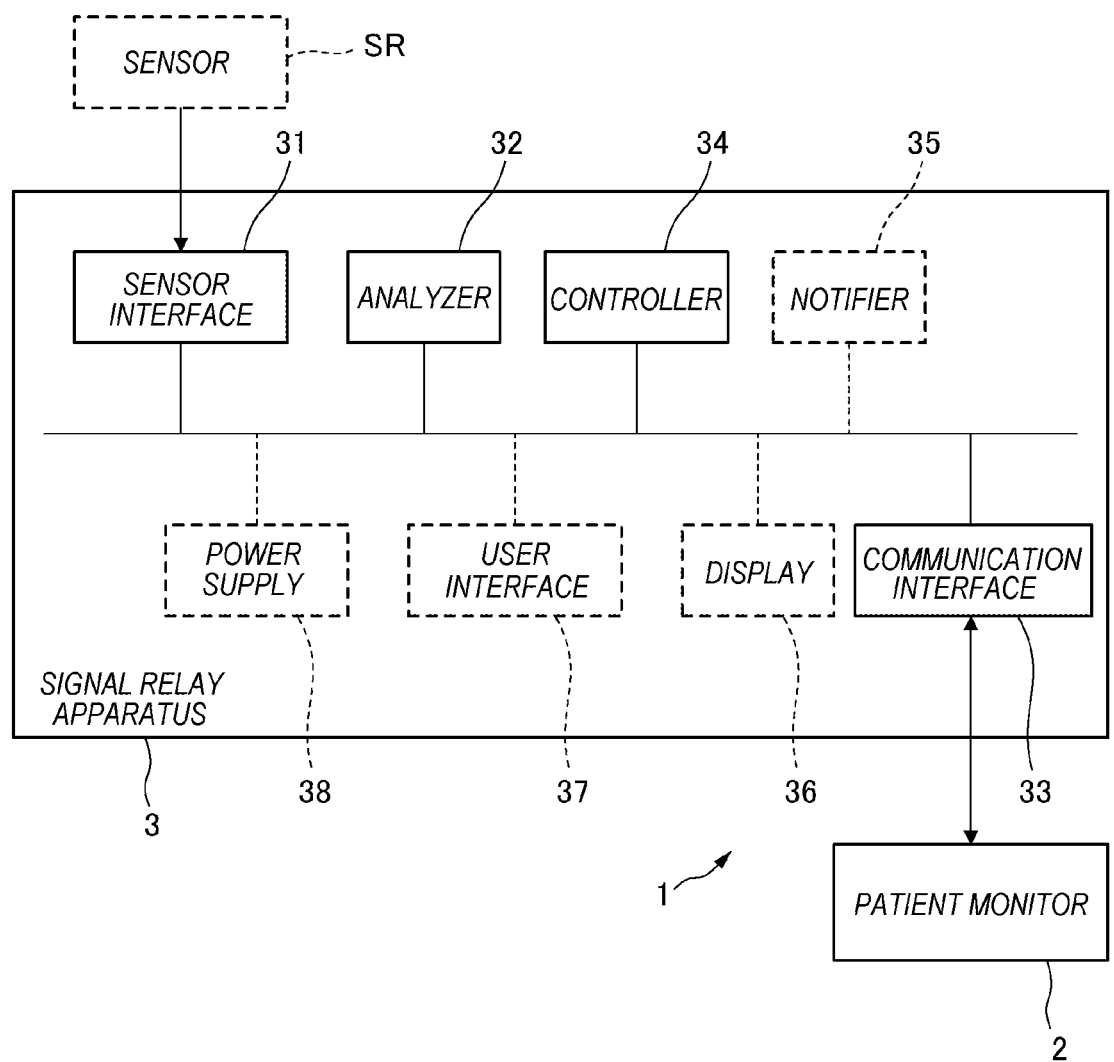
FIG. 2 illustrates a functional configuration of a signal relay apparatus of the patient monitoring system.

As illustrated in FIG. 2, the signal relay apparatus 3 may include a sensor interface 31. The sensor interface 31 is configured to receive signals output from the respective sensors SR attached to the subject S. The connections between the sensors SR and the sensor interface 31 may be performed in a wired or wireless manner.

As illustrated in FIG. 2, the signal relay apparatus 3 may include an analyzer 32. The analyzer 32 analyzes the signals input to the sensor interface 31 to acquire data corresponding to the physiological information of the subject S.

As illustrated in FIG. 2, the signal relay apparatus 3 may include a communication interface 33. The communication interface 33 is configured to allow bidirectional communication with the patient monitor 2. The communication interface 33 transmits the data acquired by the analyzer 32 to the patient monitor 2. The patient monitor 2 may be configured to reply an acknowledgement signal in response to a receipt of the data.

The patient monitor 2 performs a predetermined visualizing process based on the data supplied from the communication interface 33, and displays physiological information of the subject S on the display 21. The configuration for visualizing physiological information based on supplied data is known, and therefore its detailed description is omitted.

As illustrated in FIG. 2, the signal relay apparatus 3 may include a controller 34. The controller 34 is configured to determine whether a first abnormality condition is met. The first abnormality condition is a condition for determining that the display of physiological information on the display 21 of the patient monitor 2 is not maintained properly. Examples of the first abnormality condition include:
  physiological information not being displayed on the display 21; and
  physiological information at a specific point of time remaining to be displayed, i.e., frozen, on the display 21.
  Examples of a possible cause of such a state include:
  power cannot be supplied to the patient monitor 2 due to a power failure or the like;
  a malfunction or abnormal operation of the patient monitor 2;
  a breakage of a communication cable connecting the patient monitor 2 and the signal relay apparatus 3 to each other;
  a failure of wireless communication between the patient monitor 2 and the signal relay apparatus 3;
  an abnormality of the attachment state of one of the sensors SR; and
  a malfunction or abnormal operation of one of the sensors SR.

Therefore, for example, the controller 34 may be configured to determine whether the first abnormality condition is met by monitoring the communication between the communication interface 33 and the patient monitor 2. If it is determined that the condition of communication being established between the communication interface 33 and the patient monitor 2 is not maintained properly, it is determined that the first abnormality condition is met. Examples of a condition under which it is determined that the condition of communication being established between the communication interface 33 and the patient monitor 2 is not maintained properly include:
  a period of time during which the communication is continuously interrupted exceeds a threshold;
  an accumulated period of time during which the communication is interrupted exceeds a threshold; and
  the number of interruptions of the communication within a predetermined period of time exceeds a threshold.

The controller 34 may determine that the communication is interrupted when, for example, an acknowledgement signal from the patient monitor 2 in response to a receipt of data transmitted to the patient monitor 2 from the communication interface 33 is not received.

Whether the first abnormality condition is met may be determined by monitoring a status signal indicating the operation status of the patient monitor 2. It may be determined that the first abnormality condition is met, when the status signal indicates an abnormal operation of the patient monitor 2, or when the status signal itself cannot be acquired.

Whether the first abnormality condition is met may be determined by monitoring sensor signals input to the sensor interface 31 from the sensors SR. It may be determined that the first abnormality condition is met, when the level of the sensor signal is not within a normal range, or when the sensor signal itself cannot be acquired.

The controller 34 is configured to perform a notification (a first notification) if it is determined that the first abnormality condition is met. For example, the signal relay apparatus 3 may include a notifier 35. The notifier 35 may have a well-known configuration which can perform at least one of visual notification, audible notification, and haptic notification. In this case, the controller 34 is caused to perform at least one of visual notification, audible notification, and haptic notification, thereby notifying the user that physiological information is not properly displayed on the display 21 of the patient monitor 2.

The communication interface 33 may be configured to allow communication with an external apparatus other than the patient monitor 2. In this case, if it is determined that the first abnormality condition is met, the controller 34 can transmit a notifying signal to the external apparatus through the communication interface 33. When the external apparatus receives the notifying signal, the external apparatus notifies the user that physiological information is not properly displayed on the display 21 of the patient monitor 2, by using at least one of visual notification, audible notification, and haptic notification.

According to the above-described configuration, the user who receives the notification can immediately take an action to continue the monitoring of physiological information. Even in the case where physiological information is not properly displayed on the patient monitor 2, therefore, it is possible to enable the monitoring of the physiological information of the subject S to be continued by using the signal relay apparatus 3.

The signal relay apparatus 3 may include a display 36. The display 36 may include a liquid crystal displaying device or an organic EL displaying device.

In this case, if it is determined that the first abnormality condition is met, the controller 34 causes physiological information of the subject S to be displayed on the display 36 based on the data acquired by the analyzer 32. This is also an example of the notification. That is, physiological information to be displayed on the display 21 of the patient monitor 2 when the communication between the patient monitor 2 and the signal relay apparatus 3 is established, is displayed on the display 36 of the signal relay apparatus 3. The fact that physiological information is displayed on the display 36 notifies the user that the physiological information is not properly displayed on the patient monitor 2.

Figure 3:
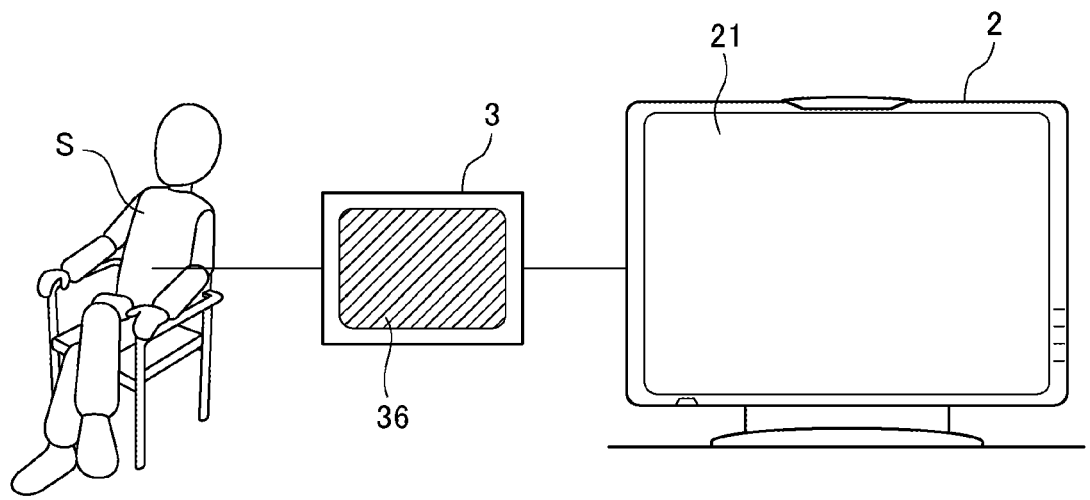
FIG. 3 illustrates an operation example of the patient monitoring system.
Figure 3:
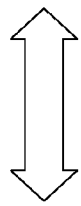
Figure 3:
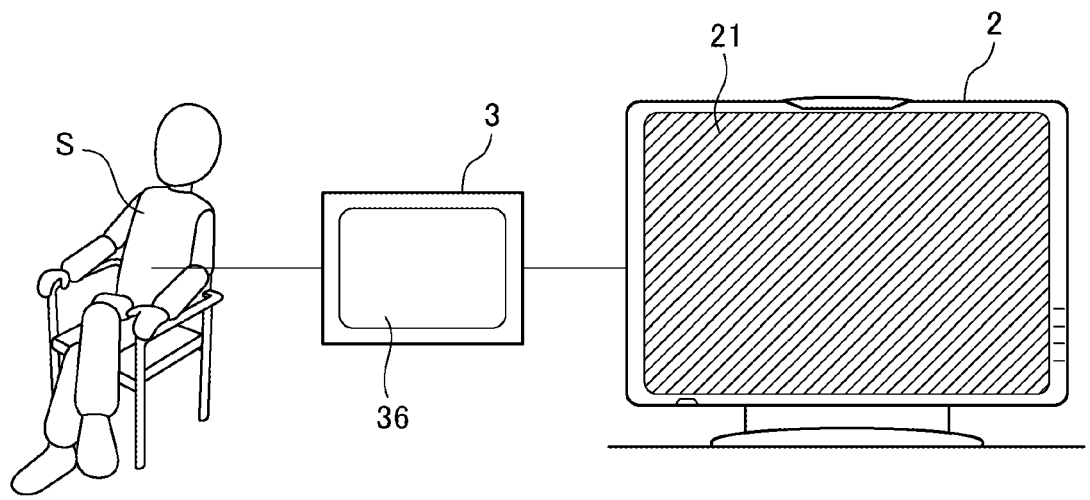

The upper section of FIG. 3 illustrates a state in which the sensors SR (not shown) attached to the subject S and the signal relay apparatus 3 are connected to each other, and the signal relay apparatus 3 and the patient monitor 2 are connected to each other. Physiological information is displayed on the display 21 of the patient monitor 2. The display 36 of the signal relay apparatus 3 is in a non-displaying state.

The lower section of FIG. 3 illustrates a state in which the physiological information is not properly displayed on the display 21 of the patient monitor 2. That is, the first abnormality condition is met. Therefore, physiological information to be displayed on the display 21 of the properly operating patient monitor 2 is displayed on the display 36 of the signal relay apparatus 3.

According to the configuration, even in the case where physiological information cannot be properly displayed on the display 21 of the patient monitor 2, the physiological information is provided through the display 36 of the signal relay apparatus 3. Also in the case where physiological information is cannot be properly displayed on the patient monitor 2, therefore, the monitoring of the physiological information of the subject S can be continued by using the signal relay apparatus 3.

If it is determined that the first abnormality condition is resolved, the controller 34 may stop the display of physiological information on the display 36.

According to the configuration, physiological information can be avoided from being duplicatively displayed, and therefore the power consumption of the signal relay apparatus 3 can be suppressed.

The notifier 35 illustrated in FIG. 2 is configured to perform a notification (a a second notification) when at least one of the signals received by the sensor interface 31 and the data acquired by the analyzer 32 meets a second abnormality condition with the physiological information being displayed on the display 36. The second abnormality condition is a condition for determining that the value of one of physiological parameters of the subject S correlated to the signals or the data is not within a normal range. For each of the physiological parameters, the thresholds for defining the normal range relating to the second abnormality condition are adequately determined.

Specifically, the analyzer 32 determines whether at least one of the signals and the data meets the second abnormality condition. If the analyzer 32 determines that the second abnormality condition is met, the controller 34 causes the notifier 35 to perform notification. The notification is performed by using at least one of visual notification, audible notification, and haptic notification. In the case where the heart rate of the subject S is not within the normal range, for example, the notifier 35 performs at least one of an alarm display and alarm sound output which indicate an abnormality in the heart rate.

According to the configuration, the signal relay apparatus 3 is caused to perform at least part of the notifying function that is usually provided in the patient monitor 2. Also in the case where physiological information is not properly displayed on the patient monitor 2, therefore, an abnormality which occurs in the physiological parameters of the subject S can be notified to the user.

As illustrated in FIG. 2, the signal relay apparatus 3 may include a user interface 37. The user interface 37 is configured to receive, while the physiological information is displayed on the display 36, an operation that replaces at least one operation to be performed on the patient monitor 2. Examples of the user interface 37 include a physical button or lever, a touchable button displayed on the display 36, and a voice recognition interface.

According to this configuration, even in the case where physiological information is not properly displayed on the patient monitor 2, part of the function of the patient monitor 2 requiring an operation input can be reproduced on the signal relay apparatus 3. This can support the continuation of the monitoring of physiological information in an unexpected situation.

Figure 4:
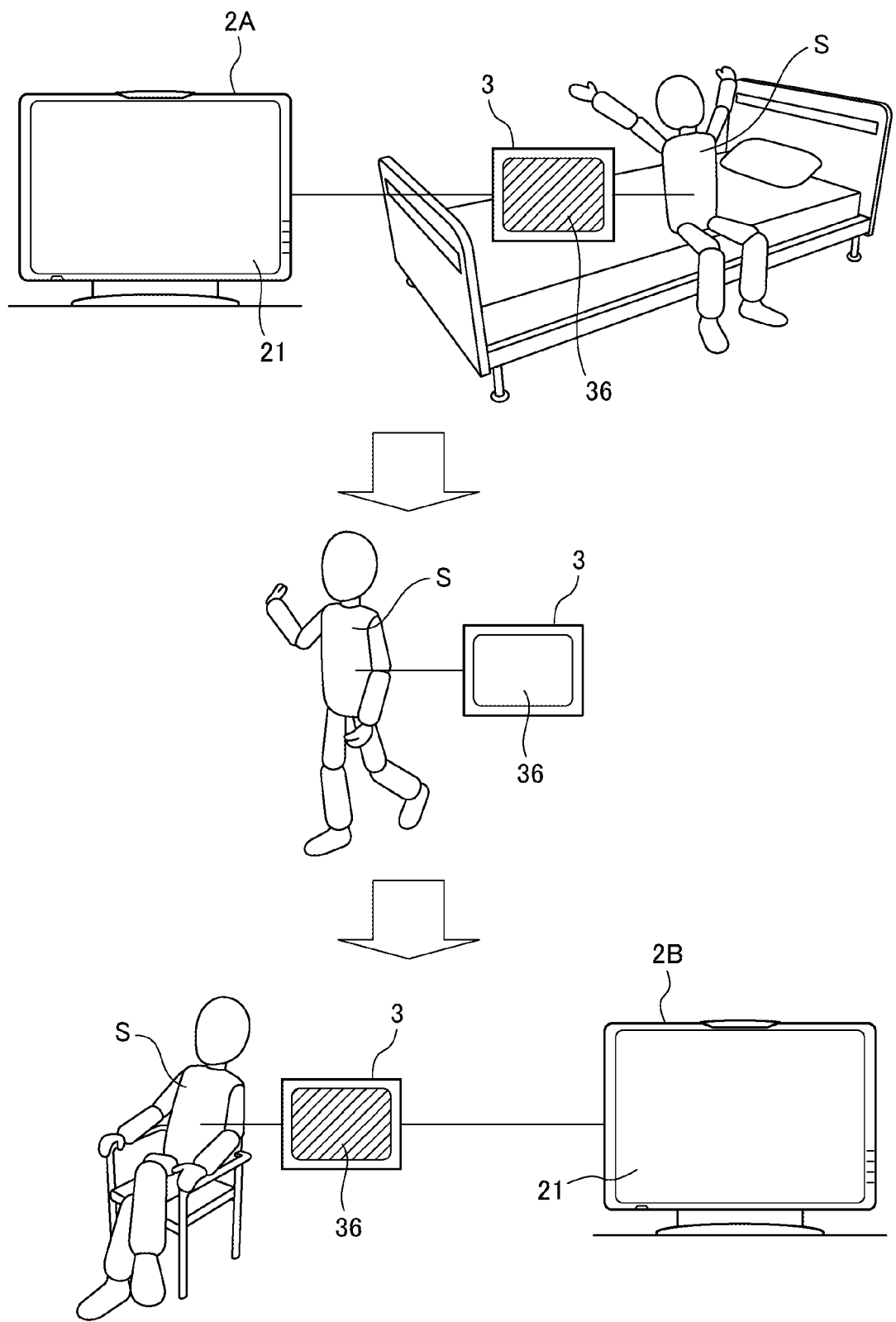
FIG. 4 illustrates another operation example of the patient monitoring system.

In addition to an unexpected situation, also when the subject S moves between different patient monitors 2 as illustrated in FIG. 4, there is a case where a power supply from the outside is interrupted. Specifically, the subject S is initially in the vicinity of a first patient monitor 2A. The signal relay apparatus 3 is connected to the first patient monitor 2A, and physiological information is properly displayed on the display 21. Therefore, physiological information is not displayed on the display 36 of the signal relay apparatus 3.

A second patient monitor 2B is disposed in a place remote from the first patient monitor 2A. In the case where the subject S moves to the place where the second patient monitor 2B is disposed, the connection between the signal relay apparatus 3 and the first patient monitor 2A is intentionally cancelled. Also in this case, physiological information is not displayed on the display 21 of the first patient monitor 2A, and therefore the controller 34 determines that the first abnormality condition is met. Consequently, physiological information is displayed on the display 36 so that the monitoring of physiological information of the subject S can be continued also while the subject S is moving.

When the signal relay apparatus 3 is connected to the second patient monitor 2B, physiological information is properly displayed on the display 21 of the second patient monitor 2B. Therefore, the controller 34 determines that the first abnormality condition is resolved. In this case, the controller 34 may stop the display of physiological information on the display 36.

According to the configuration, physiological information can be avoided from being duplicatively displayed, and therefore the power consumption of the signal relay apparatus 3 can be suppressed.

Physiological information to be displayed on the display 21 of the patient monitor 2 may include first physiological information which is relatively higher in urgency, and second physiological information which is relatively lower in urgency. The first physiological information is used primarily for observing the condition of the subject S. The second physiological information is used primarily for examining and diagnosing the subject S.

Examples of the first physiological information include:
at least one of a waveform and a numerical value, indicating one or more physiological parameters such as an electrocardiogram, brains waves, heart rate, non-invasive blood pressure, and non-invasive arterial oxygen saturation ($SpO_2$);
at least one of a waveform and a numerical value, indicating one or more parameters relating to a cardiac output; and
whether there is arrhythmia.

Examples of the second physiological information include:
a standard 12-lead electrocardiogram or a synthesized 18-lead electrocardiogram;
an evoked potential in an electrocardiogram or an electromyogram;
a polygraph; and
prognostic information and/or diagnosis assistance information based on data analysis.

In this case, the analyzer 32 of the signal relay apparatus 3 may be configured to acquire data corresponding to the above-described first physiological information. The signal relay apparatus 3 may transfer at least one of a signal and data necessary for displaying the first and second physiological information, to the patient monitor 2. The patient monitor 2 receiving at least one of the signal and the data displays both the first and second physiological information on the display 21. The signal relay apparatus 3 displays the first physiological information acquired by the analyzer 32 on the display 36.

For example, the signal relay apparatus 3 may transmit, to the patient monitor 2, only the data corresponding to the first physiological information acquired by the analyzer 32. In addition or alternatively, the signal relay apparatus 3 may transmit the signal supplied from the sensors SR to the patient monitor 2. The patient monitor 2 may acquire at least one of the first and second physiological information based on the signal. For example, while the communication between the patient monitor 2 and the signal relay apparatus 3 is normal, the signal supplied from the sensors SR may be transferred to the patient monitor 2 without performing the acquisition of the first physiological information by the analyzer 32, and the acquisition of the first and second physiological information may be performed in the patient monitor 2. In this case, when the controller 34 determines that the first abnormality condition is met, the acquisition of the first physiological information by the analyzer 32 is started.

According to the configuration, monitoring of physiological information that is higher in necessity can be continued in the case of an unexpected situation. Moreover, physiological information having a higher degree of necessity can be displayed on the display 36 in which the display region is limited as compared to the display 21 of the patient monitor 2. Furthermore, the calculation load in the analyzer 32 can be reduced to the minimum necessary, and therefore the power consumption of the signal relay apparatus 3 can be suppressed.

As illustrated in FIG. 2, the signal relay apparatus 3 may include a power supply 38. The power supply 38 is configured to, independently from the patient monitor 2, be able to supply an electric power to necessary places of the signal relay apparatus 3. Examples of the power supply 38 are a disposal battery, a rechargeable battery which can be charged by an electric power that is supplied from a commercial power supply or the patient monitor 2, and a power supply circuit which, independently from the patient monitor 2, can supply an electric power that is supplied from a commercial power supply.

In the case where the power supply 38 is configured by a disposal battery or a rechargeable battery, even when the power supply from the outside is interrupted, the monitoring of physiological information of the subject S can be continued. Examples of a cause of such a situation are interruption of power supply, a failure of the patient monitor 2, and breakage of a cable which supplies electric power to the signal relay apparatus 3 from the patient monitor 2. In this case, the controller 34 may be configured to detect interruption of the power supply from the outside, and cause the power supply 38 to start the power supply.

According to the configuration, also during a time period in which the subject moves to the second patient monitor 2B, and in which the power supply from the outside is interrupted as described with reference to FIG. 4, the monitoring of physiological information of the subject S can be continued by using the electric power supplied from the power supply 38.

In the case where the power supply 38 is configured by a power supply circuit which, independently from the patient monitor 2, can supply an electric power that is supplied from a commercial power supply, even when the power supply from the patient monitor 2 is interrupted, the monitoring of physiological information of the subject S can be continued without worrying about the battery remaining charge amount. Examples of a cause of such a situation are a failure of the patient monitor 2, and breakage of the cable which supplies electric power to the signal relay apparatus 3 from the patient monitor 2.

At least a part of the above-described functions of the analyzer 32 and the controller 34 may be realized by at least one processor and a memory. Examples of the processor are a CPU and an MPU. The processor may have a plurality of processor cores. Examples of the memory are a ROM and a RAM. Programs for realizing the above-described functions may be stored in the ROM. The processor may designate at least a part of programs stored in the ROM, develop the designated programs in the RAM, and realize the above-described functions in cooperation with the RAM.

At least a part of the above-described functions of the analyzer 32 and the controller 34 may be realized by at least one hardware (e.g., an integrated circuit such as an ASIC or an FPGA) that is different from the processor and memory that have been described above.

While the presently disclosed subject matter has been described with reference to a certain embodiment thereof for facilitating understanding of the presently disclosed subject matter, the scope of the presently disclosed subject matter n is not limited to the embodiments described above, and it will be understood by those skilled in the art that various changes and modifications may be made therein without departing from the scope as defined by the appended claims.

In the example in which the physiological information displayed on the display 21 of the patient monitor 2 contains the first and second physiological information, the first physiological information may be displayed on the display 36 of the signal relay apparatus 3 while the first and second physiological information are displayed on the display 21 of the patient monitor 2.

In this case, it is possible to realize a usage manner in which, even when the user is in a place where the user can hardly see the display 21 of the patient monitor 2, the status of the subject S can be known by referring the display 36 of the signal relay apparatus 3. By contrast, it is possible to realize another usage manner in which, in the case where the user can refer to both the display 21 and the display 36, the status of the subject S can be known more correctly by referring as required the second physiological information which includes more detailed contents.

In the example which has been described with reference to FIG. 3, while physiological information is properly displayed on the display 21 of the patient monitor 2, the display 36 of the signal relay apparatus 3 is set to a non-displaying state. However, in so far as the fact that physiological information is not properly displayed on the patient monitor 2 can be notified through the notifier 35 or the like, the display 36 may be always set to a displaying state.

What is claimed is:
1. A signal relay apparatus comprising:
   a sensor interface configured to receive a sensor signal from a sensor attached to a subject;
   an analyzer configured to analyze the sensor signal to acquire data corresponding to physiological information of the subject;

a communication interface configured to transmit at least one of the sensor signal and the data to a patient monitor;
a controller configured to perform a first notification when a display of the physiological information on the patient monitor meets a first abnormality condition;
a display device, wherein the controller is configured to cause the display device to display, as the first notification, the physiological information based on the data; and
a user interface configured to receive, while the physiological information is displayed on the display device, an operation that replaces at least one operation to be performed on the patient monitor,
wherein the first abnormality condition is a condition for determining that the display of the physiological information on the patient monitor is not maintained properly.

2. The signal relay apparatus according to claim 1, further comprising a notifier configured to perform a second notification when at least one of the sensor signal and the data meets a second abnormality condition with the physiological information being displayed on the display device.

3. The signal relay apparatus according to claim 1, wherein the controller is configured to stop displaying the physiological information on the display device when the first abnormality condition is resolved.

4. The signal relay apparatus according to claim 1,
wherein the physiological information to be displayed on the patient monitor includes first physiological information and second physiological information, the first physiological information being higher in urgency than the second physiological information, and
wherein the analyzer is configured to acquire the data corresponding to the first physiological information.

5. The signal relay apparatus according to claim 1, further comprising a power supply configured to supply electric power independently from the patient monitor.

6. The signal relay apparatus according to claim 1, wherein the controller is configured to monitor a communication between the communication interface and the patient monitor to determine whether the first abnormality condition is met.

7. The signal relay apparatus according to claim 6, wherein the controller is configured to determine that the first abnormality condition is met when one of following conditions is met:
a period of time during which the communication is continuously interrupted exceeds a first threshold;
an accumulated period of time during which the communication is interrupted exceeds a second threshold; and
a number of interruptions of the communication within a predetermined period of time exceeds a third threshold.

8. The signal relay apparatus according to claim 7, wherein the controller is configured to determine that the communication is interrupted when an acknowledgement signal from the patient monitor in response to a receipt of the data transmitted to the patient monitor from the communication interface is not received.

9. The signal relay apparatus according to claim 1, wherein the controller is configured to monitor a status signal indicating an operation status of the patient monitor to determine whether the first abnormality condition is met.

10. The signal relay apparatus according to claim 9, wherein the controller is configured to determine that the first abnormality condition is met when the status signal indicates an abnormal operation of the patient monitor, or when the status signal is not received.

11. The signal relay apparatus according to claim 1, wherein the controller is configured to monitor the sensor signal input to the sensor interface from the sensor to determine whether the first abnormality condition is met.

12. The signal relay apparatus according to claim 11, wherein the controller is configured to determine that the first abnormality condition is met when a level of the sensor signal is not within a predetermined range, or when the sensor signal is not received.

13. A signal relay apparatus configured to communicate with a patient monitor configured to display first physiological information of a subject and second physiological information of the subject, the signal relay apparatus comprising:
a sensor interface configured to receive a signal from a sensor attached to the subject;
an analyzer configured to analyze the signal to acquire data corresponding to the first physiological information;
a communication interface configured to transmit at least one of the signal and the data to the patient monitor;
a display configured to display the first physiological information while the first physiological information and the second physiological information are displayed on the patient monitor; and
a user interface configured to receive, while the first physiological information is displayed on the display, an operation that replaces at least one operation to be performed on the patient monitor.

14. A patient monitoring system comprising:
a patient monitor configured to display first physiological information of a subject and second physiological information of the subject; and
a signal relay apparatus configured to communicate with the patient monitor,
wherein the signal relay apparatus comprises:
a sensor interface configured to receive a signal from a sensor attached to the subject;
an analyzer configured to analyze the signal to acquire data corresponding to the first physiological information;
a communication interface configured to transmit at least one of the signal and the data to the patient monitor; and
a display configured to display the first physiological information while the first physiological information and the second physiological information are displayed on the patient monitor,
wherein the first physiological information is higher in urgency than the second physiological information, and
wherein the analyzer is configured to acquire the data corresponding to the first physiological information.

15. A signal relay apparatus comprising:
a sensor interface configured to receive a sensor signal from a sensor attached to a subject;
an analyzer configured to analyze the sensor signal to acquire data corresponding to physiological information of the subject;
a communication interface configured to transmit at least one of the sensor signal and the data to a patient monitor; and
a controller configured to perform a first notification when a display of the physiological information on the patient monitor meets a first abnormality condition, wherein the first abnormality condition is a condition for determining that the display of the physiological information on the patient monitor is not maintained properly, wherein the physiological information to be displayed on the patient monitor includes first physiological information and second physiological information, the first physiological information being higher in urgency than the second physiological information, and wherein the analyzer is configured to acquire the data corresponding to the first physiological information.

16. A signal relay apparatus comprising:

a sensor interface configured to receive a sensor signal from a sensor attached to a subject;

an analyzer configured to analyze the sensor signal to acquire data corresponding to physiological information of the subject;

a communication interface configured to transmit at least one of the sensor signal and the data to a patient monitor; and a controller configured to:
  perform a first notification when a display of the physiological information on the patient monitor meets a first abnormality condition, wherein the first abnormality condition is a condition for determining that the display of the physiological information on the patient monitor is not maintained properly;

monitor a communication between the communication interface and the patient monitor to determine whether the first abnormality condition is met; and determine that the first abnormality condition is met when:
    a period of time during which the communication is continuously interrupted exceeds a first threshold;
    an accumulated period of time during which the communication is interrupted exceeds a second threshold; or
    a number of interruptions of the communication within a predetermined period of time exceeds a third threshold.

17. A signal relay apparatus comprising:

a sensor interface configured to receive a sensor signal from a sensor attached to a subject;

an analyzer configured to analyze the sensor signal to acquire data corresponding to physiological information of the subject;

a communication interface configured to transmit at least one of the sensor signal and the data to a patient monitor; and a controller configured to:
  perform a first notification when a display of the physiological information on the patient monitor meets a first abnormality condition, wherein the first abnormality condition is a condition for determining that the display of the physiological information on the patient monitor is not maintained properly, wherein the display is switched between a displaying state and a non-displaying state based on whether a notification that the physiological information is displayed on the patient monitor is provided.

18. A signal relay apparatus configured to communicate with a patient monitor configured to display first physiological information of a subject and second physiological information of the subject, the signal relay apparatus comprising:

a sensor interface configured to receive a signal from a sensor attached to the subject;

an analyzer configured to analyze the signal to acquire data corresponding to the first physiological information;

a communication interface configured to transmit at least one of the signal and the data to the patient monitor; and a display configured to display the first physiological information while the first physiological information and the second physiological information are displayed on the patient monitor, wherein the display is switched between a displaying state and a non-displaying state based on whether a notification that the first physiological information and the second physiological information are displayed on the patient monitor is provided.

* * * * *